(12) United States Patent
Averous et al.

(10) Patent No.: US 8,834,572 B2
(45) Date of Patent: Sep. 16, 2014

(54) ARTHRODESIS IMPLANT

(75) Inventors: Christophe Averous, Mittelhausbergen (FR); Christophe Cermolacce, Marseilles (FR); Patrice Determe, Toulouse (FR); Patrice Diebold, Nancy (FR); Stephane Guillo, Bordeaux (FR); Hubert Rocher, Pessac (FR); Christophe Roy, Chatuzange le Goubet (FR)

(73) Assignee: Synchro Medical (FR)

( * ) Notice: Subject to any disclaimer, the term of this patent is extended or adjusted under 35 U.S.C. 154(b) by 108 days.

(21) Appl. No.: 13/583,685

(22) PCT Filed: Mar. 8, 2011

(86) PCT No.: PCT/FR2011/050473
§ 371 (c)(1),
(2), (4) Date: Nov. 20, 2012

(87) PCT Pub. No.: WO2011/110784
PCT Pub. Date: Sep. 15, 2011

(65) Prior Publication Data
US 2013/0066435 A1   Mar. 14, 2013

(30) Foreign Application Priority Data
Mar. 9, 2010  (FR) ...................... 10 51673

(51) Int. Cl.
*A61F 2/30* (2006.01)
*A61F 2/42* (2006.01)
*A61F 2/28* (2006.01)
*A61F 2/44* (2006.01)
*A61B 17/72* (2006.01)

(52) U.S. Cl.
CPC ......... *A61F 2/42* (2013.01); *A61F 2002/30904* (2013.01); *A61B 17/7291* (2013.01); *A61F 2002/30062* (2013.01); *A61B 17/7266* (2013.01); *A61F 2002/30171* (2013.01); *A61F 2002/30571* (2013.01); *A61F 2/4241* (2013.01); *A61F 2002/30112* (2013.01); *A61F 2002/30622* (2013.01); *A61F 2310/00011* (2013.01); *A61F 2/4225* (2013.01); *A61F 2230/006* (2013.01); *A61F 2002/30172* (2013.01); *A61F 2230/005* (2013.01); *A61B 17/7283* (2013.01); *A61F 2002/30594* (2013.01); *A61F 2002/30181* (2013.01); *A61F 2230/0004* (2013.01); *A61F 2230/0052* (2013.01); *A61B 17/7225* (2013.01); *A61F 2210/0004* (2013.01); *A61F 2002/4243* (2013.01); *A61F 2002/423* (2013.01)
USPC .................. 623/18.11; 623/21.15; 623/17.11; 623/16.11

(58) Field of Classification Search
CPC ............. A61F 2/32; A61F 2/28; A61F 2/441; A61F 2/442
USPC .................... 623/11.11, 16.11, 17–11, 18.11, 623/21.15–21.19
See application file for complete search history.

(56) References Cited

U.S. PATENT DOCUMENTS 7,041,106 B1   5/2006   Carver et al.
8,262,712 B2   9/2012   Coilard-Lavirotte et al.

FOREIGN PATENT DOCUMENTS

| DE | 1805665 A1 | 5/1970 |
| FR | 2801189 A1 | 5/2001 |
| FR | 2913876 A1 | 9/2008 |
| WO | 2006109004 A1 | 10/2006 |
| WO | 2008129214 A2 | 10/2008 |

OTHER PUBLICATIONS

International Search Report issued Jun. 20, 2011 re: PCT/FR2011/050473; citing: FR 2 913 876 A1, WO 2006/109004 A1, US 7,041,106 B1 and DE 1805 665 A1.

*Primary Examiner* — Jason-Dennis Stewart
(74) *Attorney, Agent, or Firm* — Cantor Colburn LLP

(57) ABSTRACT

The invention relates to an implant (1) for osseous fusion between two bones, including a first portion (20) having a longitudinal axis A, for being inserted in the first bone and including a first means (24) for attaching said implant in said first bone, and a second portion (30) having a longitudinal axis B, for being inserted in the second bone and including a second means (34) for attaching said implant in said second bone, said first and second portions (20, 30) being connected by a central core (40), said central core being a solid body, the cross-section of which, in a plane perpendicular to said longitudinal axis A, has the shape of a star having at least three points (41, 42, 43), said first portion having three tabs (21, 22, 23), each tab extending along said longitudinal axis A from the free end (41*a*, 42*a*, 43*a*) of one of the points of said central core.

12 Claims, 4 Drawing Sheets

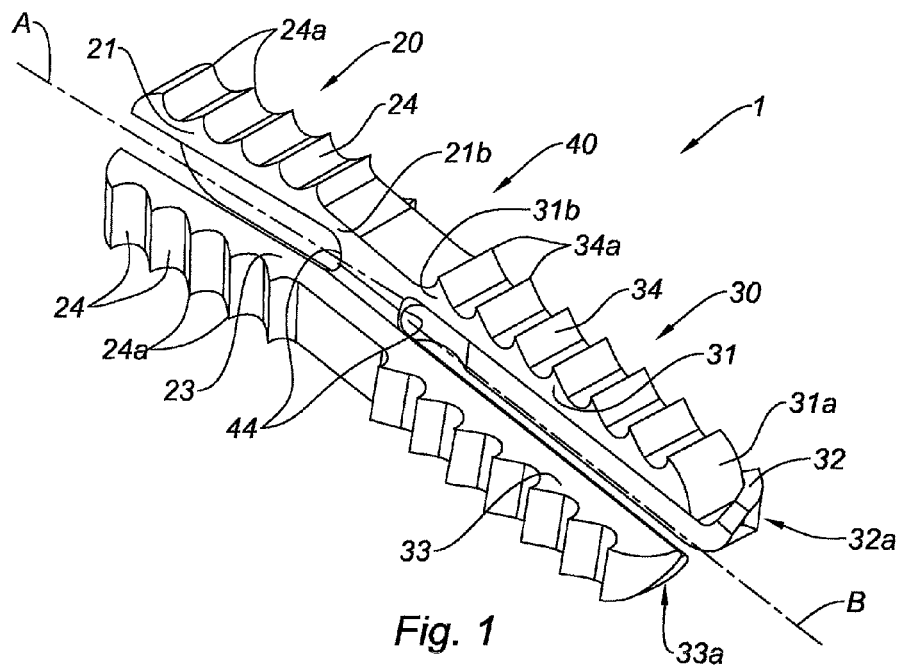
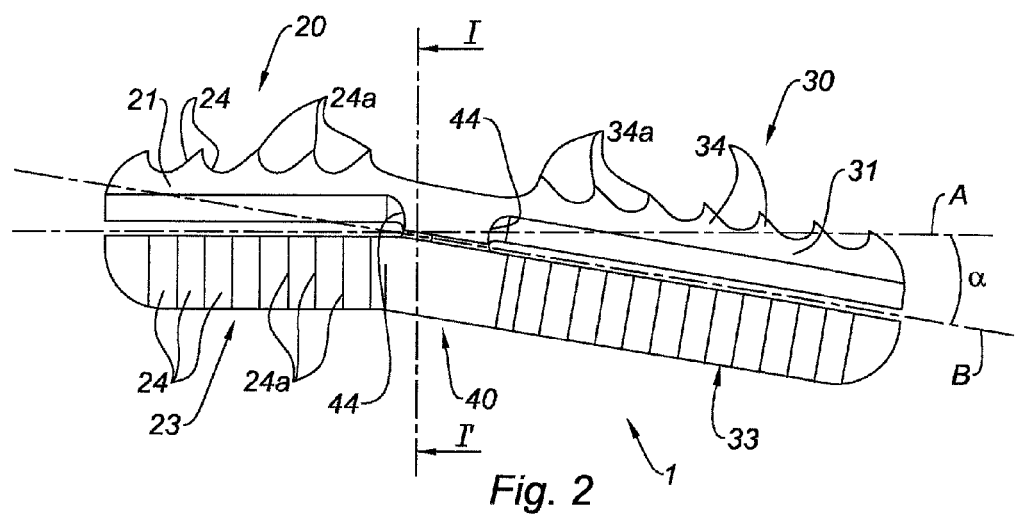

ARTHRODESIS IMPLANT

TECHNICAL FIELD

The present invention concerns a medical implant intended to connect two bones together. In particular, the invention concerns an articulated orthopedic implant for the foot or the hand, intended to connect and attach two adjacent phalanges together.

BRIEF DESCRIPTION OF RELATED ART

Certain pathologies, such as Hallux Valgus or metatarsalagias (or claw toes), induce deformation of the toes in the foot: in particular, two phalanges adjacent to a toe do not keep their natural alignment and between them form an angle permanently deforming the toe. Such deformation can take place in a vertical plane, and the patient then suffers from metatarsalgia; the toe adopts a "claw" configuration in which it is permanently tucked under. Alternatively, the deformation can take place in a horizontal plane; the patient then suffers from Hallux Valgus: the toe, in particular the big toe, forms a protuberance on the outside of the foot.

Said pathologies cause pain in the front of the foot, corns, and functional difficulties: the patient finds it difficult to walk correctly: it may also be difficult for him to wear shoes.

To correct said pathologies, it is usual to carry out an interphalangeal arthrodesis: said technique consists of surgically blocking the articulation formed by the two phalanges which have lost their natural alignment, by re-aligning them one with respect to the other and fusing them to form one single one by means of osseous fusion, the two phalanges being held together side by side by means of an implant for the period necessary for the osseous fusion.

The implant used in this type of correction therefore has two parts, one part intended to be inserted into the first phalanx, and a second part intended to be inserted into the second phalanx; the two phalanges are thus placed side by side together. The implant must allow fusion of the two bones, or phalanges, placed side by side in this manner.

Implants intended to realize interphalangeal arthrodeses have already been described. Document WO2008/129214 thus describes an implant including two opposite bony anchoring zones, each zone including two parallel points, the implant being H-shaped overall.

However, existing implants do not always ensure the necessary stability of the unit, made up by the first phalanx, the second phalanx and the implant, in the three spatial directions for the necessary time after implantation, until the two phalanges have fused together. But, if the implant or one or both of the phalanges is displaced during said lapse of time, the two phalanges will be fused together incorrectly and the treatment will fail.

It is therefore necessary for the implant, once it has been implanted, to ensure good three-dimensional stability and good support of the unit, made of the first phalanx, the second phalanx and the implant, at least until the fusion of the two phalanges together has been able to take place in the position desired by the surgeon.

BRIEF SUMMARY

The present invention proposes an implant having a structure suited to bestowing upon the implant both flexibility and rigidity allowing it to ensure, once implanted, three-dimensional stability for the unit made up of the first phalanx, the second phalanx and the implant, at least during the period necessary for osseous fusion between the two phalanges, that is to say for a duration of approximately six weeks. The implant as claimed in the invention thus allows the organ treated to have its natural anatomy restored, in particular the natural angle between the two bones or phalanges fused together again in this manner.

The present invention concerns a medical implant intended to allow osseous fusion between a first bone and a second bone, said implant including a first part with an elongated form overall and having a longitudinal axis A, intended to be inserted in the first bone and including first means for attaching said implant in said first bone, and a second part, also with an elongated form overall and having a longitudinal axis B, intended to be inserted into the second bone and including second means for attaching said implant in said second bone, said first and second parts being connected to each other by a central core, characterized in that said central core is a solid body, the cross section of which through a plane perpendicular to said longitudinal axis A, has approximately the shape of a star having at least three points, said first part having at least three tabs, each tab extending approximately along said longitudinal axis A from the free end of one of the three points of said central core.

As a result of its structure, the implant as claimed in the invention ensures, once implanted, optimum stability of the unit made up by the first bone, the second bone and the implant, for all the time necessary for the fusion between the two bones. The implant as claimed in the invention is particularly adapted to the realization of an arthrodesis between two phalanges of the foot or the hand. The first part, with an elongated shape, of the implant as claimed in the invention is intended to be inserted, for example, in the medullar canal of a first phalanx, and the second part, also with an elongated shape, of the implant as claimed in the invention, is intended to be inserted into the medullar canal of the second phalanx, adjacent to the first one. Thanks to its specific structure, in particular thanks to the presence of three tabs in the first part of the implant, each extending from a point of the solid central core, the implant as claimed in the invention assures perfect stability in the three spatial directions for the unit produced by the first phalanx, the second phalanx and the implant, and in the position required by the surgeon at the time of implantation. Moreover, the solid body central core of the implant as claimed in the invention assures both rigidity and flexibility of the implant, allowing the implant to be placed in position in an easy manner and allowing the unit, made up by the first bone, the second bone and the implant, to be supported in a reliable manner in a determined position.

As claimed in the present application, the term "shape of a star with at least three points", refers to a shape having a junction point from which extend, approximately radially, at least three points, said points being separated from each other by regular or irregular angles. For example, in one embodiment, said cross section of said central core is T-shaped: in such a case, the three points of the T are spaced apart from each other by different angles, namely two angles of 90° and one angle of 180°. In another embodiment, said cross section of said central core is Y-shaped. In other embodiments, the cross section of the central core is in the form of stars with more than three points, for example with four or five points.

The central core of the implant as claimed in the invention is a solid body: thus, the junction point of the star is made up of material. In one embodiment, said implant is monobloc. The implant as claimed in the invention can be formed of a material selected from amongst polyetheretherketones (PEEK), titanium, stainless steel, polylactic acids and their mixtures. For example, the implant as claimed in the invention can be bioresorbable or non bioresorbable.

The implant as claimed in the invention can, for example, be realized by injection molding, or even by machining.

In one embodiment, said tabs being in the form overall of an elongated parallelepiped, at least one tab has a reduced cross section at its junction with the central core. Preferably, the three tabs each have a reduced cross section at their junction with the central core. Such an embodiment allows the implant to be bestowed upon with elasticity and a flexibility allowing it to be placed in position easily. Moreover, as a result of the solid structure of the central core, the implant keeps a rigidity allowing it to ensure good stability for the unit, made up by the first bone, the second bone and the implant, at the site of implantation.

In one embodiment, said second part has at least two legs extending along the longitudinal axis B from said central core. As an alternative to this, said second part has three legs extending along the longitudinal axis B from said central core.

In one embodiment, the cross section of said central core through a plane perpendicular to said longitudinal axis B having approximately said shape of a star with at least three points, each said leg extends approximately along said longitudinal axis B from the free end of one of the points of said central core.

Such an embodiment allows the stability to be reinforced in three spatial directions of the unit, made up by the first bone, the second bone and the implant, in the position required by the surgeon, once the implant has been implanted and the two bones to be fused have been positioned side by side.

In one embodiment, said legs having overall the shape of an elongated parallelepiped, each leg has a reduced cross section at its junction with the central core. As previously seen, such an embodiment allows the implant to be bestowed upon with elasticity and a flexibility allowing it to be placed easily in position. Moreover, as a result of the solid structure of the central core, the implant keeps a rigidity allowing it to ensure good stability of the unit, made up by the first bone, the second bone and the implant, at the site of implantation.

In one embodiment, said first attachment means include locking catches located on said tabs. For example, said locking catches are located on the exterior surfaces of the parallelepipeds forming said tabs so that said tabs are fixed in the bone in which they have been inserted. Likewise, said second attaching means can include locking catches located on said legs, for example on the exterior surfaces of the parallelepipeds forming said legs so that said legs are fixed in the bone in which they have been inserted. The locking catches preferably have edges directed toward the central core so as to press each bone in the direction of the other bone, against which it is placed side by side when the implant as claimed in the invention is implanted.

BRIEF DESCRIPTION OF THE DRAWINGS

The advantages of the present invention will be seen more clearly from the description below and from the attached drawings, in which:

FIG. 1 is a perspective view of an embodiment of the implant as claimed in the invention, FIG. 2 is a side view of the implant of FIG. 1.

DETAILED DESCRIPTION

Figure 3:
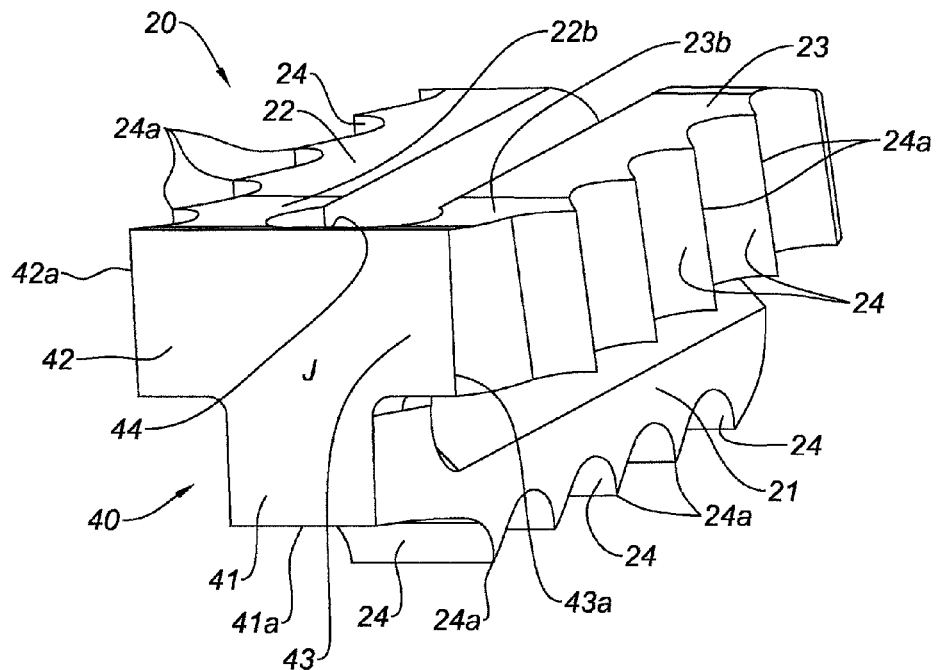
FIG. 3 is a perspective, sectioned view along the plane II' of FIG. 2 of the first part of the implant of FIG. 1.

FIGS. 1 to 3 show an implant 1 as claimed in the invention for realizing an arthrodesis. The implant 1 includes a first part 20, with an elongated shape overall, having a longitudinal axis A, a second part 30, also with an elongated shape overall and having a longitudinal axis B, and a central core 40 connecting the first part 20 to the second part 30. In the example shown, the longitudinal axis A and the longitudinal axis B form between them an angle α: said angle α can vary by about 0 to 30°, for example from 10 to 20°, in particular in order to adjust the implant of the invention to the anatomy of the part of the human body to be treated, for example the foot or the hand. In one embodiment not shown, the angle α can be zero: in such a case, the first part and the second part are located in line with one another.

As can be seen in FIG. 3, the central core 40 is a solid body, the cross section of which through the plane II' (see FIG. 2) perpendicular to the longitudinal axis A has approximately the form of a star with at least three points 41, 42, 43: in the example shown, said star is T-shaped, the point 41 corresponding to the vertical bar of the T, each point 42 and 43 corresponding in each case to an end of the cross bar of the T. Thus, each point 41, 42, and 43 extends approximately radially from one junction point shown by the letter J in FIG. 3, as far as up to the free respective end thereof (41a, 42a, 43a).

In one embodiment not shown, the star could be Y-shaped overall. As an alternative to this, the star could include more than three points. The points of the star extend approximately radially from their junction point J, and are spaced apart from each other by regular or irregular angles. In the embodiment shown in FIG. 3, the point 41 is spaced from each point 42 and 43 by an angle of 90° and the two points 42 and 43 are spaced by an angle of 180°.

Figure 4:
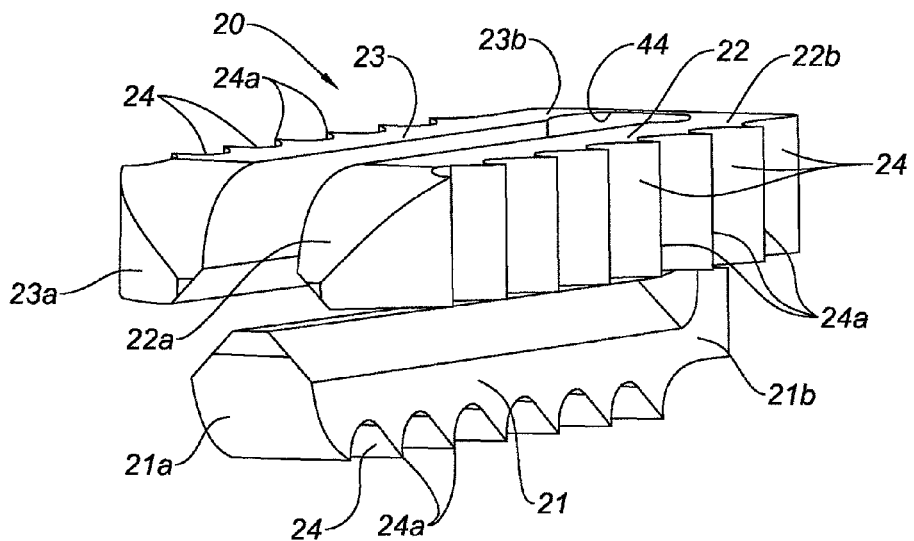
FIG. 4 is a perspective view of the rear of the first part of the implant shown in FIG. 3.

As can be seen in FIGS. 3 and 4, the first part, in the example shown, includes three tabs (21, 22, 23) each extending respectively from the free end (41a, 42a, 43a) of the three points (41, 42, 43) along the longitudinal axis A (see FIG. 1).

The tabs (21, 22, 23) all have the overall shape of an elongated parallelepiped, the free end of which (21a, 22a, 23a) is in the shape of a portion of a cone. Such a shape of the free ends (21a, 22a, 23a) of the tabs (21, 22, 23) allows for easy insertion into the bone in which the first part 20 is intended to be inserted. The section of the parallelepiped, outside the region of the free end thereof, can be overall, for example, squared, rectangular, triangular, trapezoidal. In an embodiment not shown, the tabs could have the overall form of a cylinder having an ovoid or even round sectional form. In the example shown, the three tabs (21, 22, 23) extend in parallel with respect to each other. In an embodiment not shown, the tabs (21, 22, 23) could extend along the respective axes, moving slightly away from the longitudinal axis A.

In the example shown, each tab (21, 22, 23) is provided with locking catches 24: said locking catches constitute the first attachment means intended to ensure the support of the first part 20 of the implant 1 in the bone in which said first part is intended to be inserted. From this standpoint, as shown in FIG. 2, said locking catches 24 each have an edge 24a directed toward the central core 40: as will subsequently become clear in the description below, the direction of the edges 24a toward the central core 40 helps to position the bone in which the first part is inserted side by side with the bone in which the second part 30 of the implant 1 is implanted.

Figure 5:
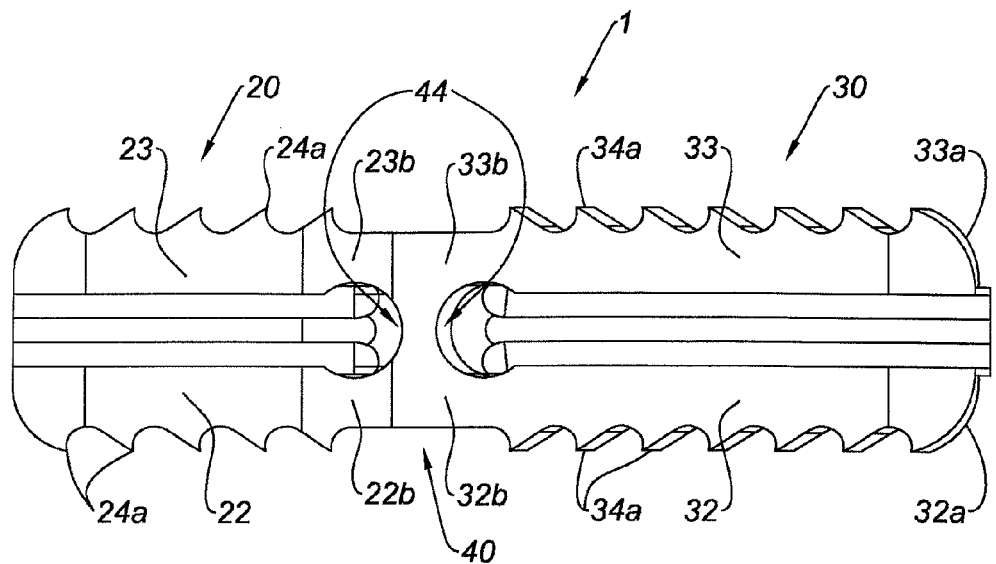
FIG. 5 is a bottom view of the implant of FIG. 1.

With reference to FIGS. 3 and 5, the three tabs (21, 22, 23) each have a reduced cross section (21b, 22b, 23b) at their junction with the central core 40. Said reduced sections (21b, 22b, 23b) form, in particular, curvilinear cuts 44 in the central core 40. Such reduced sections of the tabs, and notably the resultant curvilinear cuts 44 of the central core 40, allow the implant 1 to be bestowed upon with elasticity and a flexibility, in particular around the central core 40, allowing the implant 1 to be easily placed into position.

With reference to FIGS. 1 and 2, the second part 30, in the example shown, includes three legs (31, 32, 33) each extending respectively from the free end (41a, 42a, 43a) of the three points (41, 42, 43) of the central core 40 along the longitudinal axis B (see FIG. 1). Thus, the legs (31, 32, 33) extend overall in line, however along the longitudinal axis B of the three tabs (21, 22, 23) of the first part 20.

The legs (31, 32, 33) are all in the overall shape of an elongated parallelepiped, the free end of which (31a, 32a, 33a) is in the shape of a portion of a cone. As seen previously for the first part 20, such a shape of the free ends (31a, 32a, 33a) of the legs (31, 32, 33) allows easy insertion into the bone in which the second part 30 is intended to be inserted. The parallelepiped section, outside the region of the free end thereof, can be overall, for example, squared, rectangular, triangular, trapezoidal. In one embodiment not shown, the legs could be in the overall form of a cylinder having an ovoid or even round form section. In the example shown, the three legs (31, 32, 33) extend in parallel with each other. In one embodiment not shown, the legs (31, 32, 33) could extend along the respective axes moving slightly away from the longitudinal axis B.

In the example shown, each leg (31, 32, 33) is provided with locking catches 34: said locking catches constitute the second attachment means intended to ensure the support of the second part 30 of the implant 1 in the bone in which said second part 30 is intended to be inserted. From this standpoint, as shown in FIG. 2, said locking catches 34 each have an edge 34a directed toward the central core 40: as will subsequently become clear in the description below, the direction of the edges 34a toward the central core 40 allows the bone in which second part 30 is inserted to be pressed against the bone in which the first part 20 of the implant 1 is implanted.

With reference to FIGS. 1 and 5, the three legs (31, 32, 33) each have a reduced cross section (31b, 32b, 33b) at their junction with the central core 40. Said reduced sections (31b, 32b, 33b) form, in particular, curvilinear cuts 44 in the central core 40. As seen previously for the first part 20, such reduced sections of the legs (31, 32, 33), and notably the resultant curvilinear cuts 44 in the central core 40, allow the implant 1 to be bestowed upon with elasticity and flexibility, in particular around the central core 40, allowing the implant 1 to be easily placed in position.

In the example shown, the second part 30 has a length approximately equal to twice the length of the first part 20. Thus, the implant 1 shown in FIGS. 1 to 5 is particularly suited for an interphalangeal arthrodesis, involving two bones (a first phalanx and a second phalanx) of different lengths. In one embodiment not shown, the first part and the second part are approximately equal in length.

Figure 6:
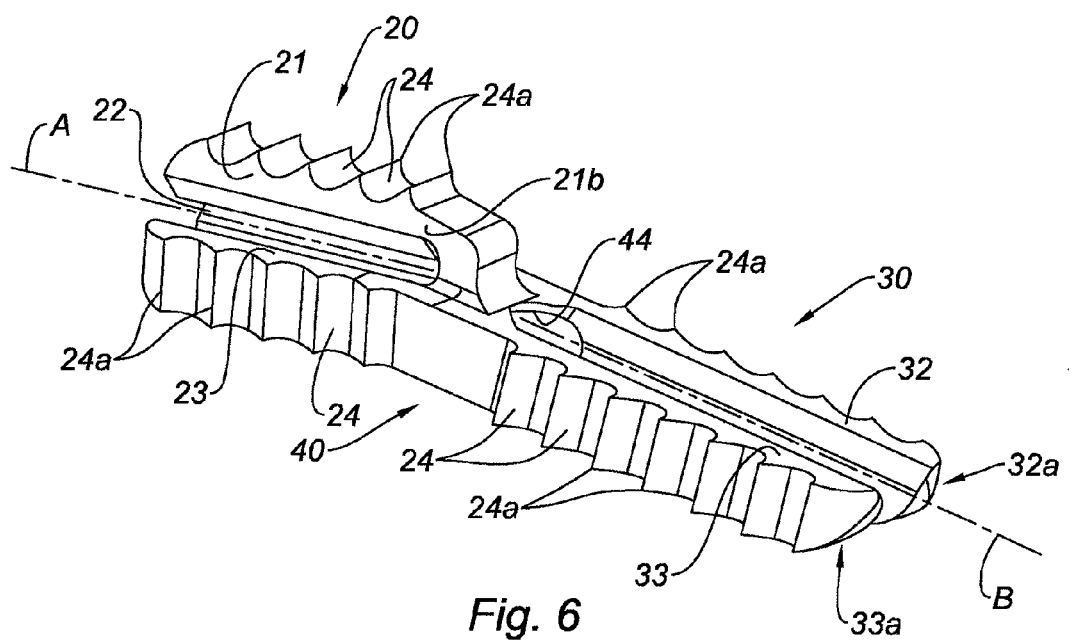
FIG. 6 is a perspective view of another embodiment of the implant as claimed in the invention.

With reference to FIG. 6, a realization variant of the implant 1 as claimed in the invention is shown in which the leg of the second part 30 extending from the free end 41a of the vertical bar of the T of the central core 40 has been dispensed with. The second part 30 thus includes two legs (32, 33), extending along the longitudinal axis B.

The implants 1 described in FIGS. 1 to 6 are preferably monobloc. They can be realized, for example, by injection molding or even by machining. The material suitable for realizing the implants 1 of said figures can be any material which is biocompatible, metallic or non-metallic. For example, said material can be selected from amongst polyetheretherketones (PEEK), titanium, stainless steel, polylactic acids, and their mixtures. Thanks to their specific structure, the implants as claimed in the invention ensure stability of the unit, made up by the first bone, the second bone and the implant, in the three spatial directions in the position required by the surgeon, whilst having good elasticity and good flexibility making them easy to manipulate and place in position.

Figure 7:
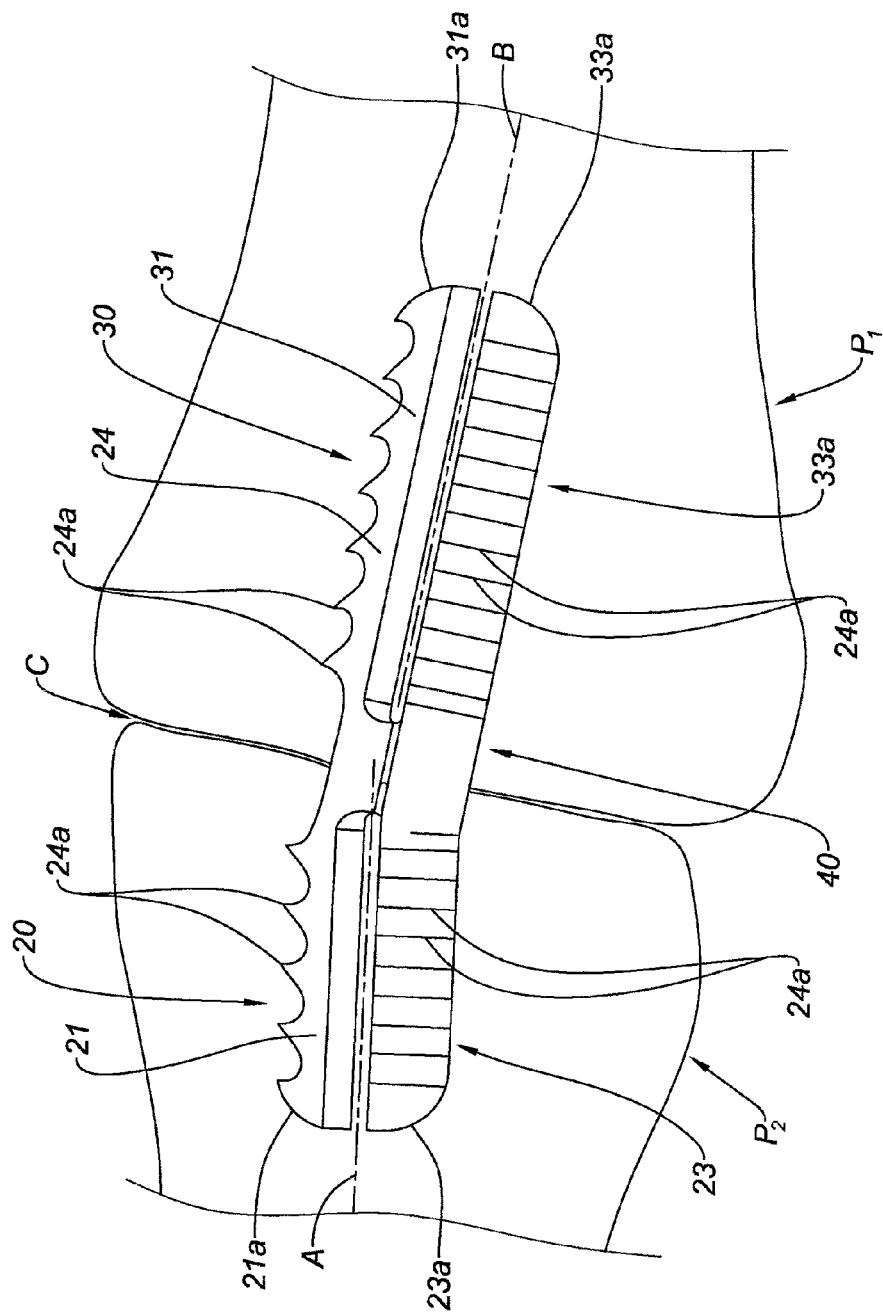
FIG. 7 is a schematic view of the implant of FIG. 1 once implanted between two bones.

FIG. 7 shows the implant 1 of FIGS. 1 to 5 once implanted, in the case of an arthrodesis concerning an articulation between two phalanges, the phalanx P1 and the phalanx P2. The implant of FIG. 6 could be used to realize an arthrodesis in the same manner.

As can be seen in FIG. 7, the first part 20 of the implant 1 has been inserted into the medullar canal of the phalanx P2 and the second part 30 of the implant 1 has been inserted into the medullar canal of the phalanx P1. In the example shown, the second part 30 being longer than the first part 20, the second part 30 has preferably been inserted into the phalanx P1 prior to the insertion of the first part 20 in the phalanx P2. In another embodiment not shown, in which the first part and the second part are approximately the same length and for which, for example, the angle α (see FIG. 2) is equal to 0°, the order in which the two parts are respectively inserted into the two phalanges to be fused can be immaterial.

With reference to FIG. 7, the respective locking catches (24, 34) of the first part 20 and of the second part 30, thanks to the respective orientation of their edges (24a, 34a), push the first bone (the phalanx P2) against the second bone (the phalanx P1) which, as can be seen in the figure, are placed together side by side. Thanks to the specific structure, the implant 1 as claimed in the invention supports the unit made up by the phalanx P1, the phalanx P2 and the implant 1 in the position determined by the surgeon, at least for the period necessary for osseous fusion between the phalanx P1 and the phalanx P2, at the initial contact surface, shown by the letter C, on the figure.

It is thus possible, thanks to the implant as claimed in the invention, to fuse the two phalanges P1 and P2 into one single one and to block the articulation between said two phalanges and to treat pathologies such as metatarsalagias or even Hallux Valgus.

The invention claimed is:

1. A medical implant intended to allow osseous fusion between a first bone and a second bone, said implant including a first part with an elongated form overall and having a first longitudinal axis, intended to be inserted in the first bone and including first means for attaching said implant in said first bone, and a second part, also with an elongated form overall and having a second longitudinal axis, intended to be inserted into the second bone and including second means for attaching said implant in said second bone, said first and second parts (20, 30) being connected to each other by a central core, wherein said central core is a solid body, the cross section of which through a plane perpendicular to said first longitudinal axis, has approximately the shape of a star having at least three points, said first part having at least three tabs, each tab extending approximately along said first longitudinal axis from the free end of one of the points of said central core.

2. The implant as claimed in claim 1, wherein said cross section of said central core is T-shaped.

3. The implant as claimed in claim 1, wherein said cross section of said central core is Y-shaped.

4. The implant as claimed in claim 1, wherein said implant is monobloc.

5. The implant as claimed in claim 1, wherein said tabs being in the form overall of an elongated parallelepiped, at least one tab has a reduced cross section at its junction with the central core.

6. The implant as claimed in claim 1, wherein said three tabs each have a reduced cross section at their junction with the central core.

7. The implant as claimed in claim 1, wherein said second part has at least two legs extending along the second longitudinal axis from said central core.

8. The implant as claimed in claim 7, wherein the cross section of said central core through a plane perpendicular to said second longitudinal axis having approximately said shape of a star with at least three points, each said leg extends approximately along said second longitudinal axis from the free end of one of the points of said central core.

9. The implant as claimed in claim 7, wherein said legs having overall the shape of an elongated parallelepiped, each leg has a reduced cross section at its junction with the central core.

10. The implant as claimed in claim 1, wherein said second part has three legs extending along the second longitudinal axis from said central core.

11. The implant as claimed in claim 1, wherein said first attachment means include locking catches located on said tabs.

12. The implant as claimed in claim 1, wherein said second attachment means include locking catches located on said legs.

* * * * *